United States Patent [19]

Ito et al.

[11] Patent Number: 5,205,293
[45] Date of Patent: Apr. 27, 1993

[54] METHOD OF MEASURING SURFACE BLOOD FLOW

[75] Inventors: Katsuki Ito, Nagoya; Kaname Ito, Chita; Shoichiro Ikeda, Nagoya; Koichi Sakurai, 101 Aza Motomachi, Ohaza Terano, Shinkawa-cho, Nishikasugai-gun, Aichi-pref., all of Japan

[73] Assignee: Koichi Sakurai, Aichi, Japan

[21] Appl. No.: 785,036

[22] Filed: Oct. 30, 1991

[51] Int. Cl.$^5$ ............................................. A61B 5/026
[52] U.S. Cl. .................................... 128/691; 128/736
[58] Field of Search ................ 128/690, 691, 734, 736

[56] References Cited

U.S. PATENT DOCUMENTS

| | | | |
|---|---|---|---|
| 4,677,985 | 7/1987 | Bro et al. | 128/691 |
| 4,802,489 | 2/1989 | Nitzan | 128/691 |

FOREIGN PATENT DOCUMENTS

| | | | |
|---|---|---|---|
| 2411392 | 8/1979 | France | 128/736 |

OTHER PUBLICATIONS

Challoner, "Accurate Measurement of Skin Blood by a Thermal Conductance Method," *Medical and Biological Engineering*, 196–201 (Mar. 1975).

*Primary Examiner*—Lee S. Cohen
*Assistant Examiner*—Brian L. Casler
*Attorney, Agent, or Firm*—Lahive & Cockfield

[57] ABSTRACT

The present invention provides a method of measuring skin blood flow on a test site using a blood flow meter. The method includes the steps of calibrating the probe of the blood flow meter, using a bio-simulating model to produce a thermo-EMF flow curve, attaching the probe to a site to be tested to generate an electromagnetic force for the test site, and determining the skin blood flow at the test site by comparing the electromagnetic force to the thermo-EMF curve. The method may also include the step of maintaining the temperature in the probe at a value slightly higher than that of the test site.

10 Claims, 6 Drawing Sheets

METHOD OF MEASURING SURFACE BLOOD FLOW

BACKGROUND OF THE INVENTION

The present invention relates to a blood flow meter for measuring blood flow on the surface of a test area by attaching a probe with plural thermocouples in series onto the test area, and also to measurement of skin blood flow with the flow meter.

An example of the system for measuring skin blood flow has been proposed by A. V. J. Challoner ('Accurate measurement of skin blood flow by a thermal conductance method'; Medical and Biological Engineering, pp 196–201; March 1975). The system includes a pair of probes with plural thermocouples and a power circuit for supplying a constant current to a heated disc of each probe. One of the probes is placed on a control or untreated site of the skin while the other on a test or treated site, and the blood flow of the test site is expressed as a difference in the thermo-EMF (electromotive force) or ratio of the readings from the two probes.

The prior system, however, can only show the blood flow on a test site as a relative value, that is, a ratio of the thermo-EMF determined by dividing the control reading by the test reading, and does not express the flow as an absolute value. Cutaneous blood flow affects the temperature of the heated disc as well as a heat-sensitive ring and varies the reference temperature of the disc, which is supposed to be constant, thus causing errors in the relationship between the thermo-EMF and the blood flow. The system also requires two probes which are attached to the test site and the control site.

SUMMARY OF THE INVENTION

The general objective of the invention is accordingly to provide a device and method of accurately measuring skin blood flow.

A specific objective of the invention is to provide a blood flow meter for measuring skin blood flow as an absolute value with only one probe.

Another specific objective of the invention is to provide accurate measurement of skin blood flow with the blood flow meter.

The above and other related objectives are realized by a blood flow meter including: a probe having a heated disc placed on the center of a heat-sensitive ring plate, and plural thermocouples arranged in series between the disc and the ring plate; a power circuit for maintaining the temperature of the heated disc at a value slightly greater than the temperature of a test site; and a measurement circuit for detecting electromotive force of the thermocouples.

Another feature of the invention is measurement of skin blood flow with the blood flow meter described above, including the steps of: attaching the probe to a bio-simulating model, which has similar thermal properties and tissues to a test site and allows accurate standard calibration of fluid flow; recording the relationship between the fluid flow and the thermo-EMF in the model detected by the measurement circuit; and comparing the thermo-EMF of the test site with the results of the standard calibration so as to determine the skin blood flow of the test site.

In the system of the invention, the temperature of the heated disc is maintained at a value slightly greater than the temperature of a test site, so that the blood flow is accurately correlated to the electromotive force. The system allows the blood flow to be expressed as an absolute value by comparing the thermo-EMF with data of the standard calibration.

BRIEF DESCRIPTION OF THE DRAWINGS

The invention may be best understood by referring to the following detailed description of the preferred embodiment and the accompanying drawings, wherein like numerals denote like elements and in which.

DESCRIPTION OF THE PREFERRED EMBODIMENT

A preferred embodiment of the invention is described according to the drawings.

Figure 1A:
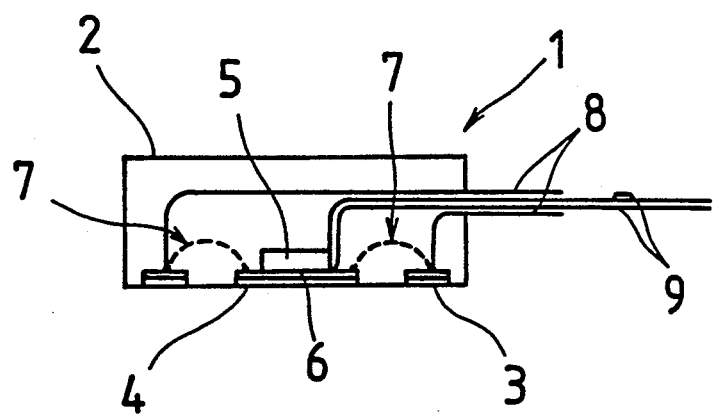
FIG. 1A is a side view illustrating the structure of a probe of a blood flow meter embodying the invention.
Figure 1B:
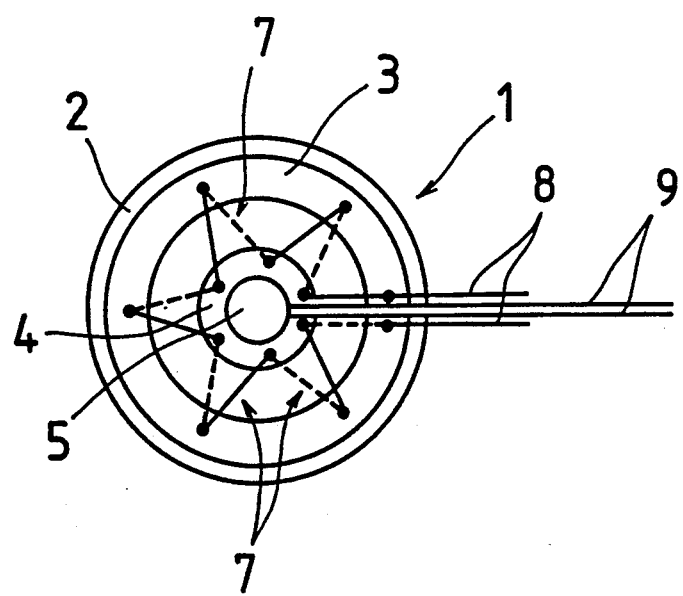
FIG. 1B is a plan view illustrating the probe of FIG. 1A.

A blood flow meter for measuring skin blood flow has a probe 1, which includes: a tubular ceramic casing 2; a heat-sensitive silver ring plate 3; and a silver heated disc 4 disposed on the center of the ring plate 3 as shown in FIGS. 1A and 1B. The ring plate 3 and the disc 4 are mounted on the bottom of the casing 2, and an oxide semiconducting ceramic heater 5 is connected to the disc 4 via an insulating sheet 6. Plural thermocouples 7,7 are radially mounted between the ring plate 3 and the disc 4 in series, and the electromotive force (hereinafter referred to as EMF) of the thermocouples is output via a compensating lead wire 8. The thermocouples 7,7, the ring plate 3, and the disc 4 are electrically insulated from one another.

Figure 2:
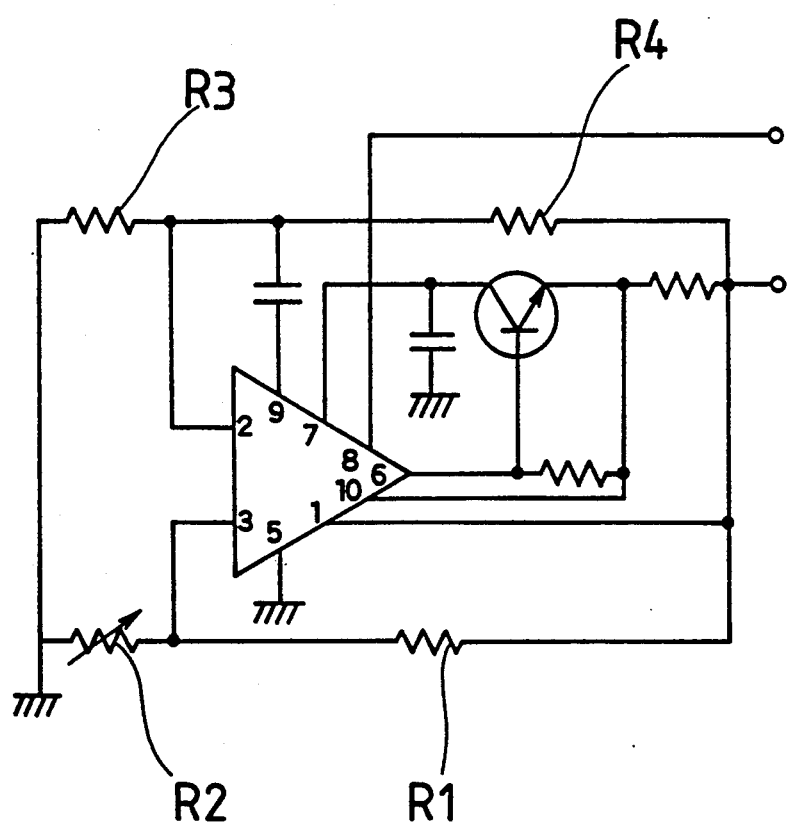
FIG. 2 is a circuit diagram showing a circuit for giving constant heating current.

The heater 5 is further connected via a lead 9 to a constant heating circuit of FIG. 2 which supplies constant direct current for maintaining the temperature of the heater 5 constant. The constant heating circuit does not include a temperature sensor but is operated correspondingly to the temperature dependence of the heater 5. A resistance R3 functioning as the heater 5 is connected to the inversion input of an IC (integrated circuit) working as an operational amplifier, and power is supplied through another resistance R4. The resistances R3 and R4 form a bridge together with resistances R1 and R2 connected to the non-inversion input of the IC, and are heated by the current. The resistance R3 with the increased capacity is maintained constant according to the equation $R1 \times R3 = R2 \times R4$, and the temperature of the resistance R3 is thus kept at a constant value determined corresponding to the thermal properties thereof.

The temperature control of the heater 5 may automatically be executed based on EMF data of the thermocouples input into a computer.

Figure 3A:
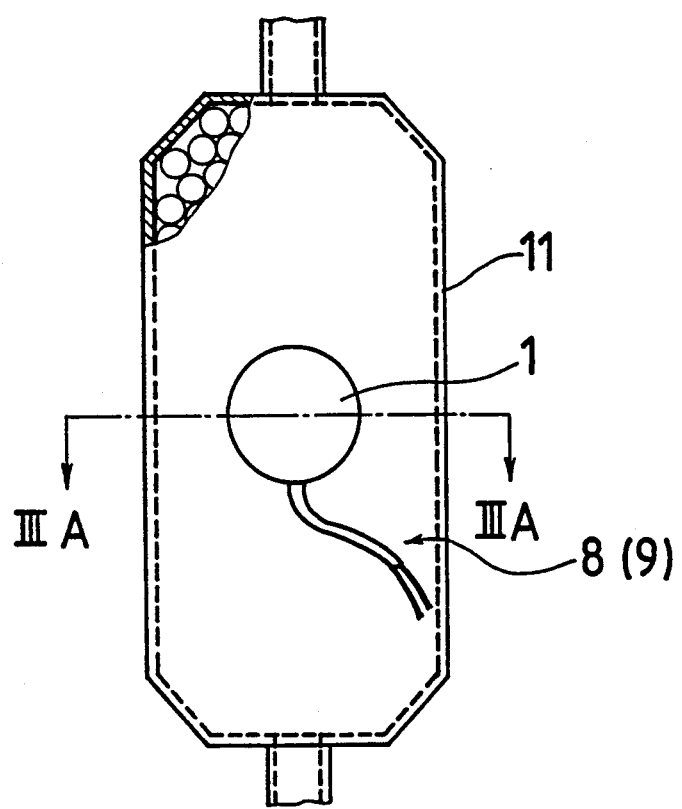
FIG. 3A is a schematic diagram showing a bio-simulating model, partially cut away.
Figure 3B:
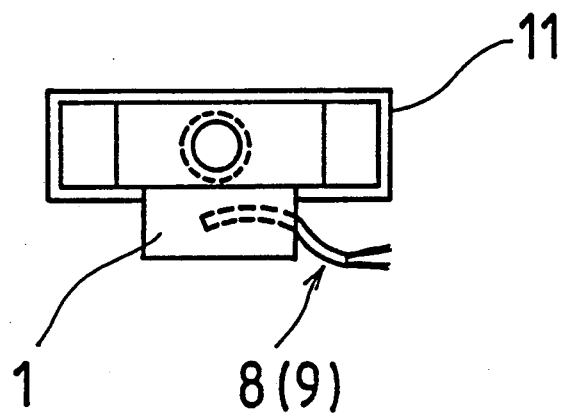
FIG. 3B is a cross sectional view illustrating the bio-simulating model taken on the line IIIA—IIIA of FIG. 3A.

The relationship between the EMF of the thermocouples 7,7 and the blood flow is determined with a bio-simulating model 10 shown in FIGS. 3A and 3B.

Figure 3C:
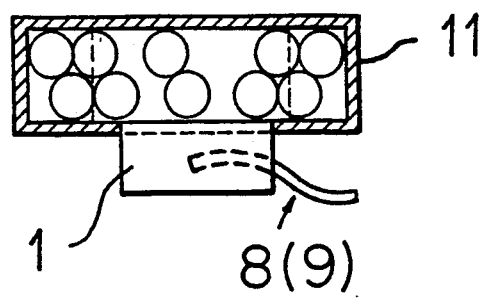
FIG. 3C is a cross sectional view illustrating an embodiment of the biosimulating model, taken on the line IIA—IIA of FIG. 3A, illustrating the small balls for preventing vortexes.

The bio-simulating model 10 includes a rectangular tube 11, which allows water flow, has an identical cross section in the direction of flow, and is filled with wooden small balls (see FIG. 3C) for preventing vortexes. The small balls are preferably made of balsa or Ochroma pyramidale (Cav.) Urban because of its high water content and specific heat similar to water. The balsa soaked in water for a long time was measured to have the specific heat of 0.95 while blood and liver have 0.91 and kidney has 0.99, and is thereby optimal material of the balls. The measurement side of the probe 1 is attached to an inner face of the rectangular tube 11. Since the content of the rectangular tube 11 is mostly water, the model 10 has thermal properties similar to those of the epidermal tissues including the specific heat. The liver is covered with a thin membrane of approximately 0.2 mm thick having the specific heat close to one. The model 10 does not allow any water flow up to the depth of 0.2 mm from the surface, and thereby well simulates the epidermal tissues of the liver.

Process of standard calibration is described hereinafter. The probe 1 is attached to the inner wall of the rectangular tube 11 in such a manner that the ring plate 3 and the disc 4 are brought into contact with fluid in the tube 11. Water warmed to the skin temperature is allowed to enter the tube 11 at the top and escape at the bottom. Electricity is supplied to the heater 5 of the probe 1 so that the temperature of the heater 5 is maintained at a value slightly higher than the water temperature. Heat is taken from the disc 4, which is heated with the heater 5, and transferred to the ring plate 3 by means of the water flow. The temperature of the heater 5 is automatically controlled to have a constant value by the constant heating circuit and thereby the temperature of the disc 4 is maintained constant, while the heat transfer raises the temperature of the ring plate 3. The heat transfer causes the temperature difference between the ring plate 3 and the disc, resulting in generation of EMF of the thermocouples 7,7. The amplified EMF is output through the arrangement of the thermocouples 7,7 connected in series.

The temperature of the heater 5 is set at a value only 1° C. higher than the water temperature to minimize the effects on blood flow.

Figure 4:
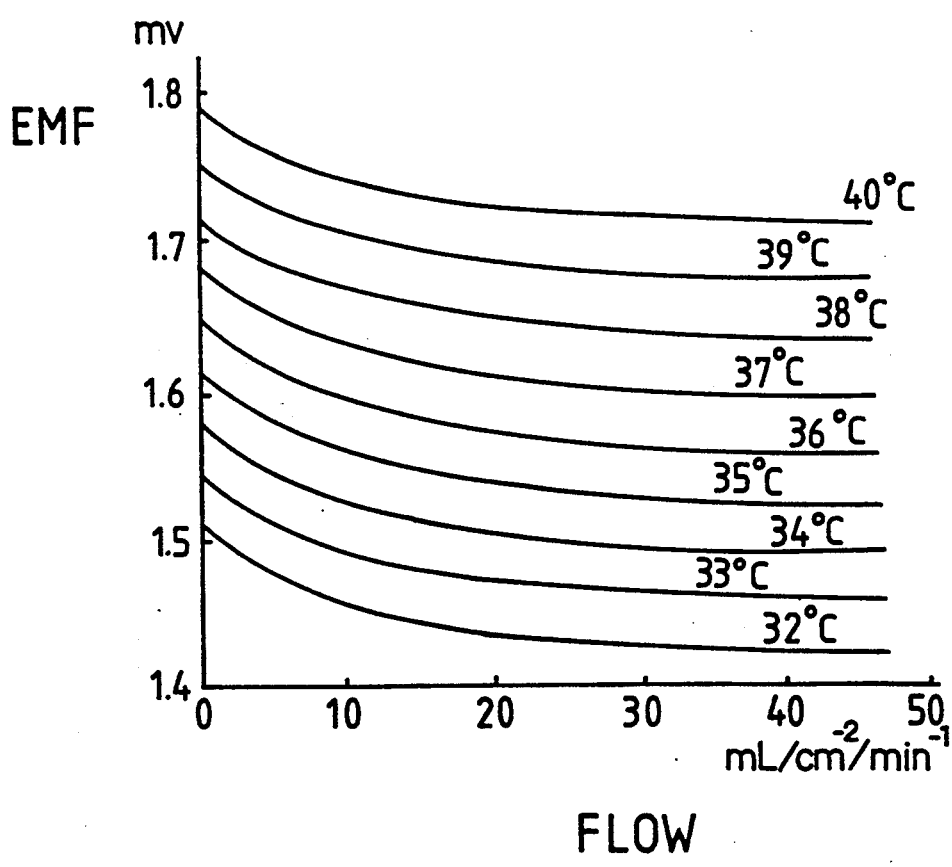
FIG. 4 is a graph showing the relationship between the flow and the electromotive force.

The same process is repeated for various water temperatures to determine standard curves of the EMF and the flow at such temperatures (see FIG. 4).

These standard curves are applicable to organs with thin epidermis like the liver since the surface of the model 10, which does not allow fluid flow and is exposed to the measurement side of the probe 1, is relatively thin and simulates only such organs. Standard curves for organs with thick surface such as kidney and skin are determined based on measurement by placing real epidermal tissues between the measurement side of the probe 1 and water.

The blood flow of a test site is determined in the following manner. The probe 1 is attached to a test site and the disc 4 is heated to a temperature 1° C. higher than the temperature of the test site to generate the EMF. The blood flow on the surface of the test site at the temperature is then read from the EMF—flow curve and determined as an absolute value.

Calculation above may be executed by a computer for enhancing accuracy and saving time; data of the standard calibration is input into the computer, and the results are displayed on a CRT (cathode ray tube).

The larger number of the thermocouples gives higher sensitivity, but twelve may be preferable considering the space and usability. The composition of the ceramic heater is selected to have the Curie temperature which causes no burn and to be usable as a temperature fuse.

Since there may be many modifications and changes without departing from the scope of the invention, the embodiment above is not intended to limit the invention to the embodiment. For example, copper disc and ring plate may be used in place of silver ones, and an organ of an animal such as a rabbit may be used as a bio-simulating model.

As described above, the system of the invention allows determination of surface blood flow as an absolute value, and thus has following surgical effects:

(1) Data of the surface blood flow on the implanted liver or kidney is practical for evaluation of the operation and further treatment;

(2) Measurement of terminal blood flow in implanted blood vessel is applicable to further treatment;

(3) The cause of a shock resulting in drop in blood pressure may be inferred from data of the surface blood flow;

(4) Data of terminal blood flow is used as a supplementary condition for determining amputation in arterial or venous thrombus;

(5) Measurement of surface blood flow on inosculated joints of stomach or small or large intestines after esophagectomy prevents hemokinetic blockage; and (6) Measurement of blood flow on the liver surface serves to elucidate the metabolism of various enzymes in the liver.

What is claimed is:

1. A method of measuring skin blood flow on a test site using a blood flow meter having a probe having a heated disc, a heat-sensitive ring plate, and plural thermocouples arranged in series between said disc and said ring plate the method comprising the steps of calibrating the probe by means of a bio-simulating model, having similar thermal properties to a test site to produce a thermo-EMF flow curve, attaching the probe to a test site for generating an electromagnetic force in response to the test site, and comparing the electromagnetic force of the test site with the thermo-EMF curve produced in the calibrating step to determine the skin blood flow of the test site.

2. The method in accordance with claim 1, further comprising the step of providing said bio-simulating model with a rectangular tube filled with wooden balls.

3. The method in accordance with claim 2, further comprising the step of providing balls made of balsa or Ochroma pyramidale (Cav.) Urban.

4. A method of measuring in accordance with claim 1, wherein said calibrating step further comprises heating water in said bio-simulating model to skin temperature, and heating said disc to a temperature 1° C. higher than the water temperature.

5. A method of measuring in accordance with claim 1, wherein said attaching and generating step further comprises maintaining the temperature of said heater at a value 1° C. higher than the temperature of the test site.

6. The method of claim 5 further comprising the step of providing a power circuit for maintaining the temperature of said heated disc at a value slightly greater than the temperature of the test site.

7. The method of claim 1 further comprising the step of recording the relationship between the electromagnetic force at the test site and the thermo-EMF curve produced using the bio-simulating model.

8. A method of measuring skin blood flow on a test site using a blood flow meter, said method comprising the steps of calibrating a probe by means of a bio-simulating model having similar thermal properties to a test site, to produce a thermo-EMF flow curve, attaching the probe to a test site for generating an electromagnetic force in response to the test site, and comparing the electromagnetic force of the test site with the thermo-EMF curve produced in the calibrating step to determine the skin blood flow of the test site.

9. The method of claim 8 further comprising the step of recording the relationship between the fluid flow and the thermo-EMF in the model.

10. The method of claim 8 further comprising the step of maintaining the temperature in the probe at a value slightly greater than the temperature of the test site.

* * * * *